(12) United States Patent
Dyer et al.

(10) Patent No.: US 12,280,244 B2
(45) Date of Patent: Apr. 22, 2025

(54) ACTIVE INJECTION GUIDE

(71) Applicant: Portal Instruments, Inc., Cambridge, MA (US)

(72) Inventors: Robert J. Dyer, Cambridge, MA (US); Andrew Coats, Cambridge, MA (US); Patrick Anquetil, Cambridge, MA (US)

(73) Assignee: Portal Instruments, Inc., Cambridge, MA (US)

( * ) Notice: Subject to any disclaimer, the term of this patent is extended or adjusted under 35 U.S.C. 154(b) by 397 days.

(21) Appl. No.: 17/099,925

(22) Filed: Nov. 17, 2020

(65) Prior Publication Data

US 2021/0069418 A1   Mar. 11, 2021

Related U.S. Application Data

(63) Continuation of application No. 16/783,428, filed on Feb. 6, 2020, now abandoned, which is a continuation
(Continued)

(51) Int. Cl.
*A61M 5/30*        (2006.01)

(52) U.S. Cl.
CPC ......... *A61M 5/30* (2013.01); *A61M 2205/332* (2013.01); *A61M 2205/3331* (2013.01);
(Continued)

(58) Field of Classification Search
CPC .......... A61M 5/30; A61M 5/20; A61M 5/172; A61M 5/1723; A61M 5/31566; A61M 5/31571; A61M 2205/332; A61M 2205/215; A61M 2205/3331; A61M 2205/3344; A61M 2205/50; A61M 2205/581; A61M 2205/582; A61M 2205/583; A61M 2205/3327; A61M 2205/33; A61M 2205/0227; A61M 2205/13; A61M 2205/21; A61M 2005/208; A61M 2005/2013; A61M 2005/2073; A61M 2005/2026; A61M 2005/3022; A61M 2005/1726; A61M 2230/005;
(Continued)

(56) References Cited

U.S. PATENT DOCUMENTS

| | | | |
|---|---|---|---|
| 6,547,755 B1 * | 4/2003 | Lippe | A61M 5/20 604/154 |
| 2005/0256448 A1 * | 11/2005 | Angel | F03G 7/065 604/68 |
| 2008/0059133 A1 * | 3/2008 | Edwards | A61M 15/009 703/7 |
| 2008/0154188 A1 | 6/2008 | Hochman | |
| 2009/0216182 A1 | 8/2009 | Lauchard et al. | |

(Continued)

FOREIGN PATENT DOCUMENTS

WO   2006/116997 A1   11/2006

OTHER PUBLICATIONS

WIPO, "PCT Application No. PCT/US19/30096, International Preliminary Report on Patentability dated Nov. 12, 2020", 13 pages.

*Primary Examiner* — Joel M Attey
*Assistant Examiner* — Alexandra Lalonde
(74) *Attorney, Agent, or Firm* — Strategic Patents, P.C.

(57) ABSTRACT

An active injection guide concurrently monitors surface contact and an instantaneous contact force along an injection axis of an injector in order to ensure that the injector is properly positioned on a patient before an injection can be initiated.

20 Claims, 8 Drawing Sheets

Related U.S. Application Data of application No. 16/400,290, filed on May 1, 2019, now Pat. No. 11,400,220.

(60) Provisional application No. 62/665,004, filed on May 1, 2018.

(52) U.S. Cl.
CPC ... *A61M 2205/50* (2013.01); *A61M 2205/581* (2013.01); *A61M 2205/582* (2013.01); *A61M 2205/583* (2013.01)

(58) Field of Classification Search
CPC .. A61M 5/31; A61M 5/31565; A61M 5/3157; A61M 2005/2006; A61M 2205/3341; A61M 2205/58; A61M 5/24; A61M 5/2422; A61M 2005/2403; A61M 2005/2433; A61M 2209/08; A61M 2209/088; G09B 23/285
See application file for complete search history.

(56) References Cited

U.S. PATENT DOCUMENTS

| | | |
|---|---|---|
| 2009/0292240 A1 | 11/2009 | KraMer et al. |
| 2010/0010374 A1 | 1/2010 | Escutia et al. |
| 2010/0049126 A1 | 2/2010 | Bronfeld et al. |
| 2013/0154948 A1 | 6/2013 | Schediwy et al. |
| 2014/0107578 A1 | 4/2014 | Iwase et al. |
| 2014/0276414 A1 | 9/2014 | Baker et al. |
| 2014/0335495 A1 | 11/2014 | Baker et al. |
| 2015/0045729 A1 | 2/2015 | Denzer et al. |
| 2015/0379899 A1* | 12/2015 | Baker .................. G09B 23/285 434/262 |
| 2016/0235916 A1* | 8/2016 | Edwards ............. A61M 5/2053 |
| 2017/0049965 A1* | 2/2017 | Baker ..................... A61M 5/20 |
| 2017/0056582 A1 | 3/2017 | Niklaus |
| 2017/0281877 A1 | 10/2017 | Marlin et al. |
| 2017/0354780 A1* | 12/2017 | Park .................. A61M 5/31565 |
| 2017/0368260 A1 | 12/2017 | McCullough et al. |
| 2018/0193564 A1* | 7/2018 | Dahmani .............. A61M 5/315 |
| 2019/0262538 A1* | 8/2019 | Schabbach .............. A61M 5/24 |

\* cited by examiner

ACTIVE INJECTION GUIDE

RELATED APPLICATIONS

This application is a continuation of U.S. application Ser. No. 16/783,428, filed Feb. 6, 2020, which is a continuation of U.S. application Ser. No. 16/400,290, filed May 1, 2019, which claims priority to U.S. Provisional Application No. 62/665,004 filed on May 1, 2018, the entire content of which is hereby incorporated by reference.

BACKGROUND

While needle-free injectors can avoid some of the drawbacks associated with needles, these injectors may also impose additional constraints on correct handling of an injector, e.g., with respect to position, contact force and orientation. There remains a need for a needle-free injector that facilitates improved targeting for physical delivery of medicine.

SUMMARY

An active injection guide for an injector concurrently monitors surface contact and an instantaneous contact force along an injection axis of an injector in order to ensure that the injector is properly positioned on a patient before an injection can be initiated.

Aspects have one or more of the following advantages.

Among other advantages, aspects ensure that an injector head of the injector is properly seated on a target injection area on the patient. In some aspects, ensuring a proper seating of the injector prevents accidental ejection of injectate into a medium (e.g., the air) other than a patient by ensuring that a head of a injector is properly seated on a target injection surface (e.g., the skin of a patient's thigh) before allowing for an injection to occur. For example, conventional injector systems may allow ejection of injectate regardless of whether the injector system is properly seated on a patient. As a result, some conventional injectors are able to dangerously eject injectate into unintended targets (e.g., into the air or a patient's eye). Aspects use sensors to ensure a proper seating of the injector to avoid these drawbacks associated with some conventional injectors.

In some aspects, ensuring a proper seating of the injector ensures that injectate is injected to a proper depth into the patient's body. For example, one challenge associated with conventional injector technology is reliable delivery of a full dose of injectate into a target tissue region. This challenge is exacerbated if a desired angle of injection is other than perpendicular to the skin's surface. For example, if the desired angle of injection is 45-degrees relative to the skin surface, then an injection should only be performed when the desired angle of injection relative to the skin's surface is achieved and when a predetermined force is applied to the skin by the injector head along the desired angle of injection. When both the desired angle of injection and the predetermined force are achieved, the injector head is considered to be properly seated. Aspects advantageously take the guess work out of seating the injector head by using sensors to detect a proper seating of the injector head.

In certain embodiments, when the predetermined force applied by the nozzle of the injector head is achieved, the nozzle depresses and deforms a localized area of the contact surface such that the injection axis extends at a substantially 90° angle relative to the localized area of the contact surface. By injecting the substance at such an angle, the ability to maintain the substance within the subcutaneous layer is advantageously maximized and the risk of the injectable substance passing through to the adjacent tissue is minimized. By positioning the nozzle at an acute angle relative to the contact surface and then deforming a localized area of the contact surface such that the injection site is perpendicular to the injection axis (i.e., the injectable substance pierces the injection site at a 90° angle), the injectable substance is introduced along the subcutaneous layer rather than transverse to the layer. This approach for introducing the injectable surface is particularly advantageous because physical characteristics (i.e., thickness, hardness, elasticity, composition) vary from subject to subject. It is appreciated that although a 90° angle is preferable, there is still a benefit to injecting the substance at angles offset from 90° (e.g., in a range between 5° and 85°, or the supplements thereof).

Other features and advantages of the invention are apparent from the following description, and from the claims.

DETAILED DESCRIPTION

Embodiments will now be described with reference to the accompanying figures. The foregoing may, however, be embodied in many different forms and should not be construed as limited to the illustrated embodiments set forth herein.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated, and each separate value within such a range is incorporated into the specification as if it were individually recited herein. The words "about," "approximately" or the like, when accompanying a numerical value, are to be construed as indicating any deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose, or the like. The use of any and all examples or exemplary language ("e.g.," "such as," or the like) is intended merely to better illuminate the embodiments and does not pose a limitation on the scope of the disclosed embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms unless expressly stated otherwise.

1 ACTIVE INJECTION GUIDE

Figure 1:
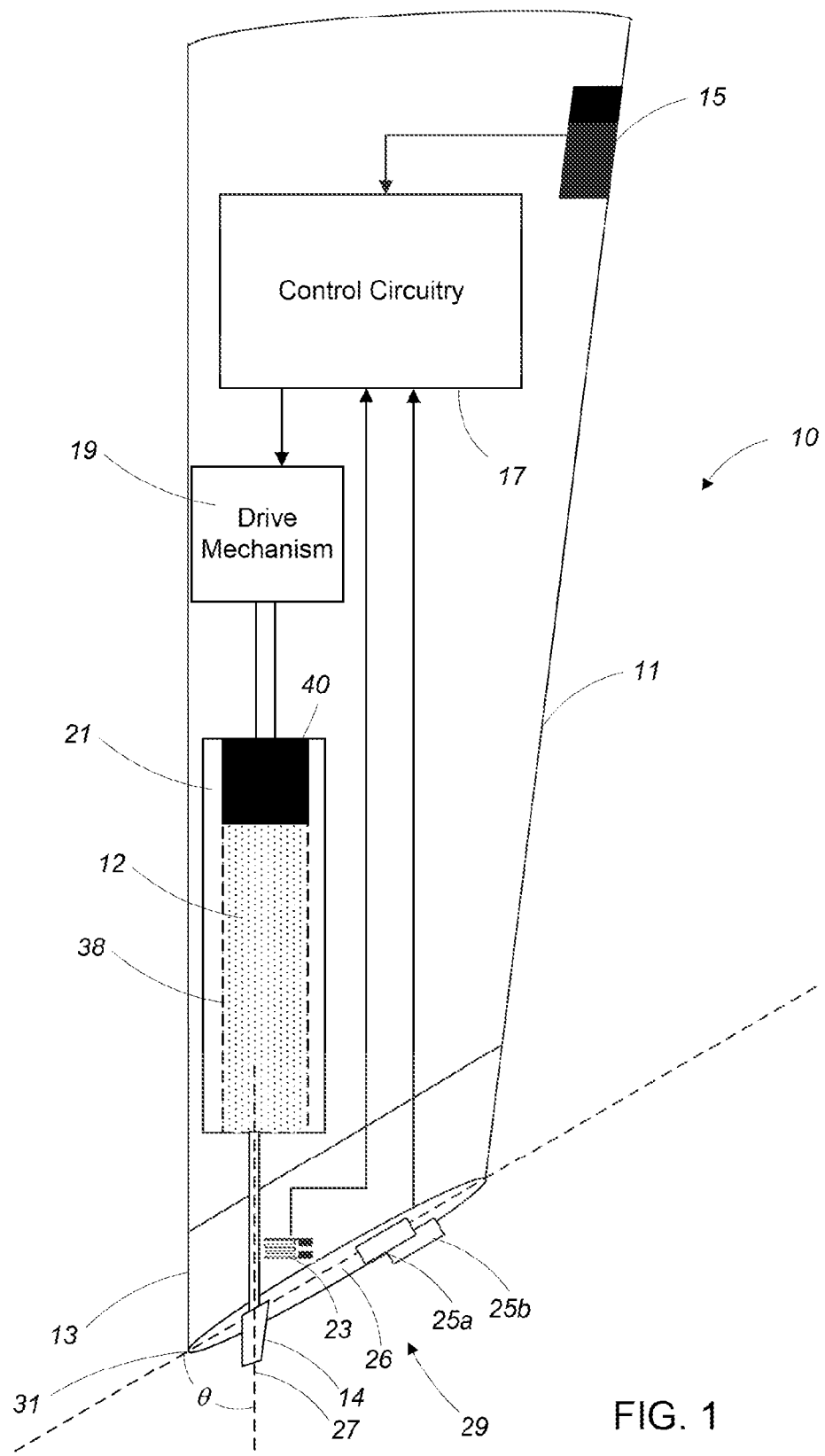
FIG. 1 shows a needle-free injector with an active injection guide.
Figure 2:
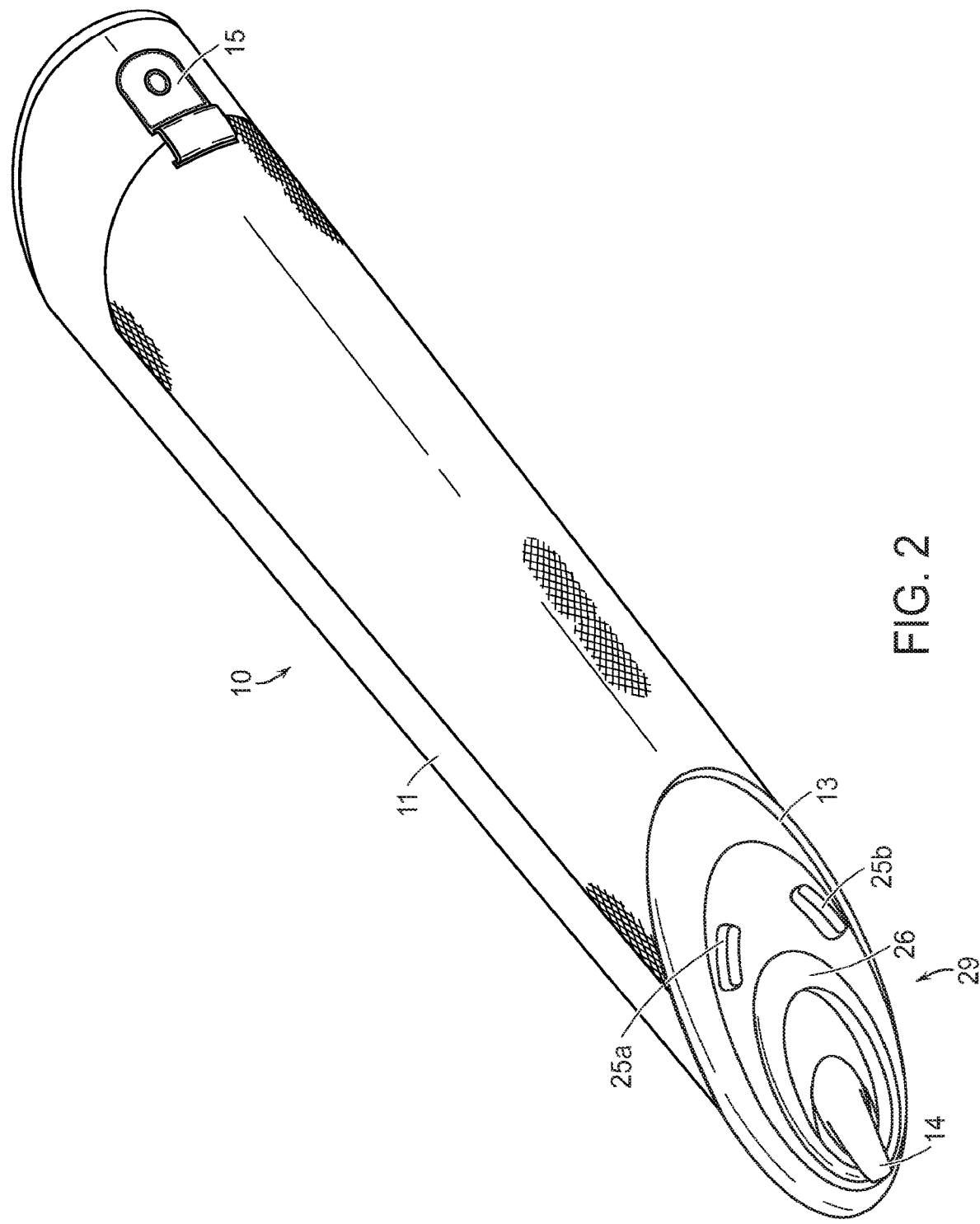
FIG. 2 is a perspective view of the needle-free injector of FIG. 1.

Referring to FIGS. 1 and 2, an injector 10 such as a needle-free injector with an active injection guide may be used to provide a patient with an injectate 12 (e.g., liquid medications, vaccines, and select solid dose implants) without the use of painful, sharp needles. While a needle-free injector is shown, it will be understood that the techniques described herein may also or instead be used with needle-based injectors such as an auto-injector or the like. Thus the injector 10 may be any type of injector unless a more specific meaning is explicitly provided or otherwise clear from the context. The injector 10 may include an enclosure 11 with an injector head 13 attached thereto.

The enclosure 11 may include a pushbutton 15 or other control input, and the enclosure 11 may generally house control circuitry 17, a drive mechanism 19 (e.g., a linear actuator), and a primary container 21. The primary container 21 may have a bore 38 for receiving the injectate 12 and may be in fluid communication with the nozzle 14. A plunger 40 may be sized and shaped for insertion into the bore 38 of the primary container 21. The drive mechanism 19 may be mechanically coupled to the plunger 40 for driving the plunger 40 into the bore 38 of the primary container 22 in a direction toward a distal end 31 of the primary container 22.

As is described in greater detail below, the control circuitry 17 may control the drive mechanism 19 according to input signals that it receives from the pushbutton 15 and sensors attached to the injector head 13. When certain input conditions (described in greater detail below) are met, the control circuitry 17 may cause the injector 10 to perform an injection, including causing the drive mechanism 19 to drive the plunger 40 into the bore 38 of the primary container 22, thus forcing injectate 12 out of the primary container 22 via the nozzle 14.

The injector head 13 may include a contact surface 26, a nozzle 14 protruding from the contact surface 26, a contact sensor 29 disposed on the contact surface 26, and a load sensor 23 that is mechanically coupled to the nozzle 14. In general, the contact surface 26 may be a substantially planar contact surface 26, or may have any other three-dimensional shape suitable for aligning to a target surface of interest. The nozzle 14 may include an orifice (not shown) through which injectate 12 is shaped and delivered to the patient along an injection axis 27. The injection axis 27 is disposed at an angle, $\theta$ relative to the contact surface 26. While the injection axis 27 may, for example, be an axis along which a jet of the injectate 12 is propelled from the injector head 13 in a needle-free injection, it will be understood that the injection axis 27 may also or instead be a central axis of an injection needle or the like extending from the injector head 13 for physical insertion under a patient's skin.

The methods and systems contemplated herein for enforcing proper orientation and force of an injector may be adapted for use with an injector using a needle, particularly where the needle positioning, orientation, and depth of penetration might have an impact on the effective therapeutic delivery of an injectate. It should also be appreciated that an injector may usefully include two or more injection axes, e.g., for delivery of large volumes of fluids or for greater dispersion of injectate. Multi-axis injectors may, for example, use multiple parallel axes, multiple divergent axes or some combination of these, and the techniques described herein may be similarly adapted for use with any such multi-axis injectors without departing from the scope of this disclosure.

In some examples, the load sensor 23 is configured to detect whether an instantaneous contact force exerted along the injection axis 27 by the nozzle 14 on a target injection surface is within a predetermined range of forces. In one aspect, the load sensor 23 may output a signal indicative of the instantaneous contact force along the injection axis 27, and the control circuitry 17 may process this measured load to determine if it is within the predetermined range of forces. In another aspect, the load sensor 23 may be configured to respond to a load exceeding a predetermined limit, e.g., by providing a binary indication that the threshold has been exceeded, or by opening or closing a switch to indicate that the threshold has been exceeded. Thus in one aspect, if the force detected by the load sensor 23 is within the predetermined range of forces, then the load sensor 23 outputs a signal indicating that the nozzle 14 is pressed into the target injection surface with an appropriate force along the injection axis 27. Otherwise, the load sensor 23 outputs a signal indicating that the nozzle 14 is not pressed into the target injection surface with an appropriate force. In some examples, the load sensor 23 includes a strain gauge. In other examples, the load sensor includes a hydraulic load cell, a piezoelectric load cell, a pneumatic load cell, or any other suitable sensor or combination of sensors that transduces a force to a corresponding electrical signal suitable for use by the control circuitry 17 to control operation of the injector 10.

In general, the contact sensor 29 is configured to detect whether the contact surface 26 is in contact with the target injection surface, e.g., in planar contact such that the injection axis 27 is properly oriented relative to a target injection surface. In some examples, the contact sensor 29 includes three or more spatially separated contact points and is configured to detect whether all of the contact points are in contact with the target injection surface. If all of the contact points are in contact with the target injection surface, then the contact sensor 29 may output a signal indicating that the contact surface 26 is in contact with the target injection surface, with the injection axis 27 properly oriented relative to the target injection surface. Otherwise, if any of the contact points are not in contact with the target injection surface, then the contact sensor 29 may output a signal indicating that the contact surface 26 is not in contact with the target injection surface, and/or that the injection axis 27 is not properly oriented relative to the target injection surface. The contact points may also or instead provided signals to the control circuitry 17 in order for the control circuitry to evaluate a current contact state.

In the embodiment of FIGS. 1 and 2, the contact sensor 29 includes three contact points: a first cleat 25a, a second cleat 25b, and the nozzle 14. Very generally, if the first cleat 25a, the second cleat 25b, and the nozzle 14 are all in contact with a target injection surface, the contact sensor 29 may indicate (or the control circuitry 17 may infer) that the contact surface 26 is in contact with the target injection surface, with the injection axis 27 properly oriented relative to the target injection surface. Otherwise, if any of the first cleat 25a, the second cleat 25b, and the nozzle 14 is not in contact with the target injection surface, then the contact sensor 29 may indicate that the contact surface 26 is not in contact with the target injection surface, and/or that the injection axis 27 is not properly oriented relative to the target injection surface.

In some examples, the first cleat 25a and the second cleat 25b are coupled to a corresponding switch (not shown) that is normally open but closes when the cleats are both in contact with (e.g., pressed against) a surface (e.g., the target injection surface). In another aspect, the state of a number of switches indicate individually whether the first cleat 25a and the second cleat 25b are in contact with the target injection surface. In one aspect, only two cleats (or other contact sensors/switches) may be used, and an axial load on the nozzle 14 may provide a separate, independent condition for permitting an injection that also implicitly confirms correct planar orientation by recording a non-zero contact force at a third location, the location of the nozzle 14. As is described above, the nozzle 14 may be mechanically coupled to the load sensor 23, and any force exceeding a predetermined contact threshold that is registered by the load sensor 23 indicates that the nozzle 14 is in contact with the target injection surface. The contact threshold may depend on the type of injection (e.g., subcutaneous, intradermal and so forth), the region of the body where the injection being made, the physical condition of the patient, the volume of the injection, and so forth. By way of non-limiting example, a useful range of thresholds for contact force may be, e.g., three to five Newtons.

It will be understood that a variety of other sensors, techniques and the like may also or instead be used as the contact sensor 29 contemplated herein. For example, the contact sensor 29 may use only two sensors (e.g., the cleats 25a, 25b), or the contact sensor 29 may be formed of a ring or the like within the plane of the contact surface 26 that is electromechanically configured to provide a signal or close a switch only when the entire ring is physically displaced, e.g., by contact with a target surface, or at a number of specific locations (e.g., at discrete locations) around the ring. The contact sensor 29 may also or instead include two or more capacitive touch sensors, a resistive circuit formed through the skin of a patient, or a single capacitive sensor formed along the ring that detects whether the entire ring is in contact with the target surface. This may also or instead include any other sensor or combination of sensors, along with suitable processing, for detecting when the contact surface 26 is in a desired orientation and planar contact with a target surface.

While the active injection guide is not separately enumerated in the accompanying drawings, it will be appreciated that the active injection guide may include any of the sensors, control circuity, and other physical and mechanical features of the injector 10 described herein that contribute to, or cooperate to provide, the monitoring and control of the injector 10 to facilitate injection with an intended position and contact force.

2 OPERATION

Figure 3:
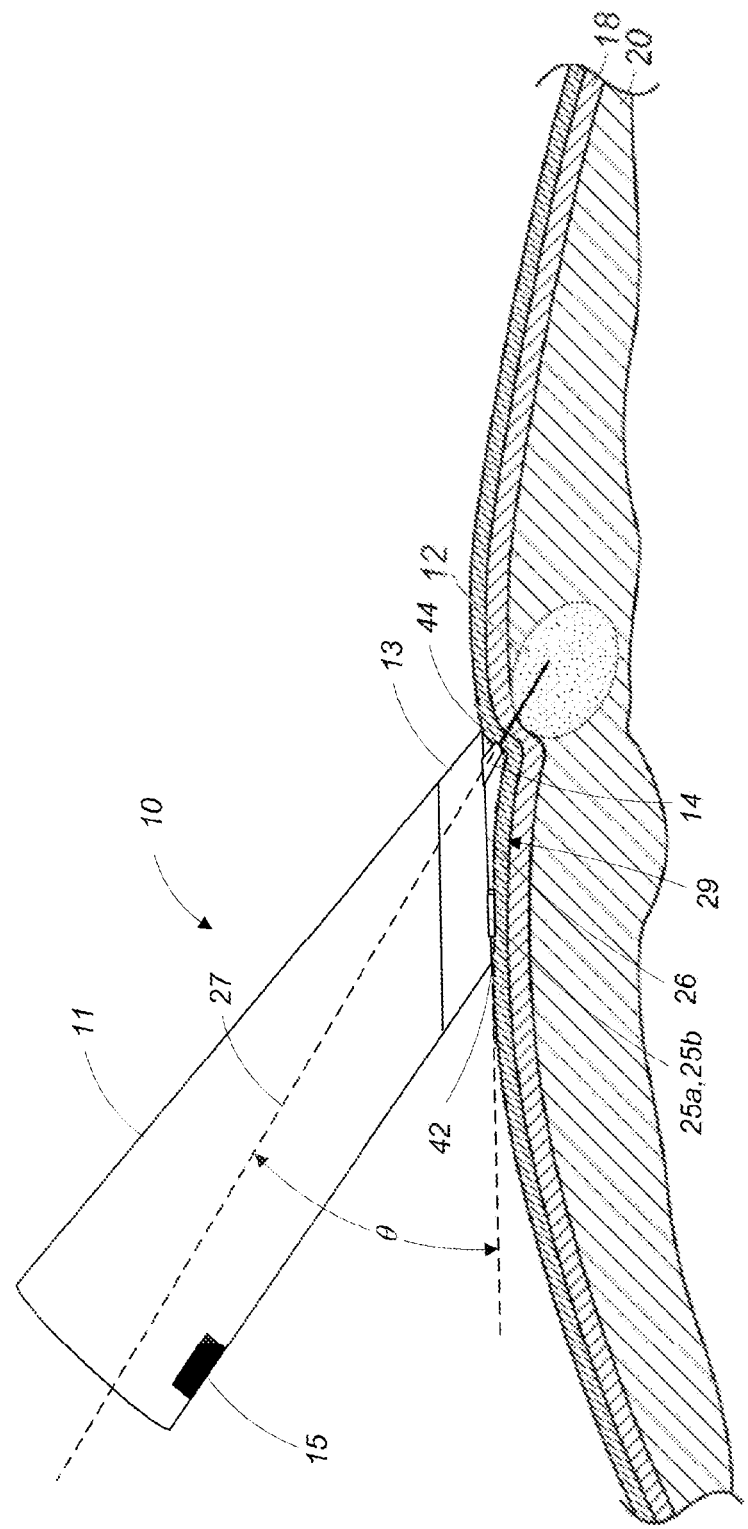
FIG. 3 shows the needle-free injector of FIG. 1 in operation.

Referring to FIG. 3, the head 13 of the injector 10 is disposed on a target injection surface 42 such as the skin of a patient. Human skin, for example, includes an epidermis 16 and a dermis 18 overlaying a subcutaneous space 20.

Very generally, the injector 10 ensures that the injector head 13 is properly seated on a target injection surface 42 before allowing an injection operation to occur. In one aspect, for the injector 10 to be properly seated on the target injection surface 42, two conditions must be satisfied: (1) the injection axis 27 must be properly oriented relative to the target injection surface 42, and (2) the nozzle 14 must contact the target injection surface 42 with sufficient axial force to properly engage with the target injection surface 42.

The first condition—proper orientation—can generally be enforced by shaping the contact surface 26 of the injector head 13 to physically mate with or rest against the target injection surface 42 in a desired manner, such as with the injection axis 27 disposed at an angle, $\theta$ within a predetermined range relative to a plane at or through the target injection surface 42. While the shape of the contact surface 26 may provide simple mechanical feedback to a user to guide the user in a tactile manner toward the correct orientation, the use of two or more contact sensors or switches (or any similar sensors or the like, as described above) may be used as control inputs to ensure the correct orientation before automated or manual initiation of an injection.

The second condition—proper axial load—can help ensure suitable positioning for injection, such as by ensuring that the injector head 13 is in firm, non-sliding engagement with the target injection surface 42, ensuring that target injection surface is sufficiently taught in the localized area 44 where an injectate will penetrate the skin, and/or that the layers of skin are properly oriented relative to the injection axis 27 (e.g., so that the target injection surface is substantially perpendicular to, or at a substantially 90° angle to, the injection axis 27 in the localized area 44 where the injection axis 27 intersects the target injection surface 42 as depicted in FIG. 3). In order to enforce a proper axial load concurrently with proper orientation, one or more sensors may be provided as generally contemplated herein to measure an instantaneous contact force along the injection axis 27 at the same time that contact sensors or the like monitor for correct global orientation of the injector 10 to the target injection surface.

The control circuitry 17 of the injector 10 may monitor signals from the contact sensor 29 and the load sensor 23 on the injector head 13 to determine whether the two conditions are satisfied. For example, to satisfy the first condition, the contact sensor 29 may sense that the contact surface 26 is in contact with the target injection surface 42 with the injection axis 27 correctly oriented relative to the target injection surface 42. For example, the contact sensor 29 of FIGS. 1 and 2 may detect that the cleats 25a, 25b and the nozzle 14 are in contact with the target injection surface 42. To satisfy the second condition, the load sensor 23 may sense that a force applied to the localized area 44 of the target injection surface 42 by the nozzle 14 along the injection axis 27 is within a predetermined range of forces that are known to achieve the desired deformation in the localized area 44 of the target injection surface 42.

When the contact sensor 29 senses that the first condition is met and the load sensor 23 senses that the second condition is met, the control circuitry 17 of the injector 10 may determine that the injector head 13 is properly seated on the target injection surface 42, and permit a user to initiate an injection operation, e.g., by pressing the pushbutton 15. In another aspect, the control circuitry 17 may be configured to automatically initiate an injection when the two injection conditions are satisfied, or, for example, when the two injection conditions remain satisfied for a predetermined interval. Other conditions or sensed states may also or instead be used in combination with these injection conditions to provide additional control or safety measures. In another aspect, the control circuitry 17 may initiate any type of suitable user feedback such as with a buzzer, flashing LED, beep or other auditory, visual or tactile feedback to indicate that the injector 10 is ready for operation.

3 CONTROL CIRCUITRY

Figure 4:
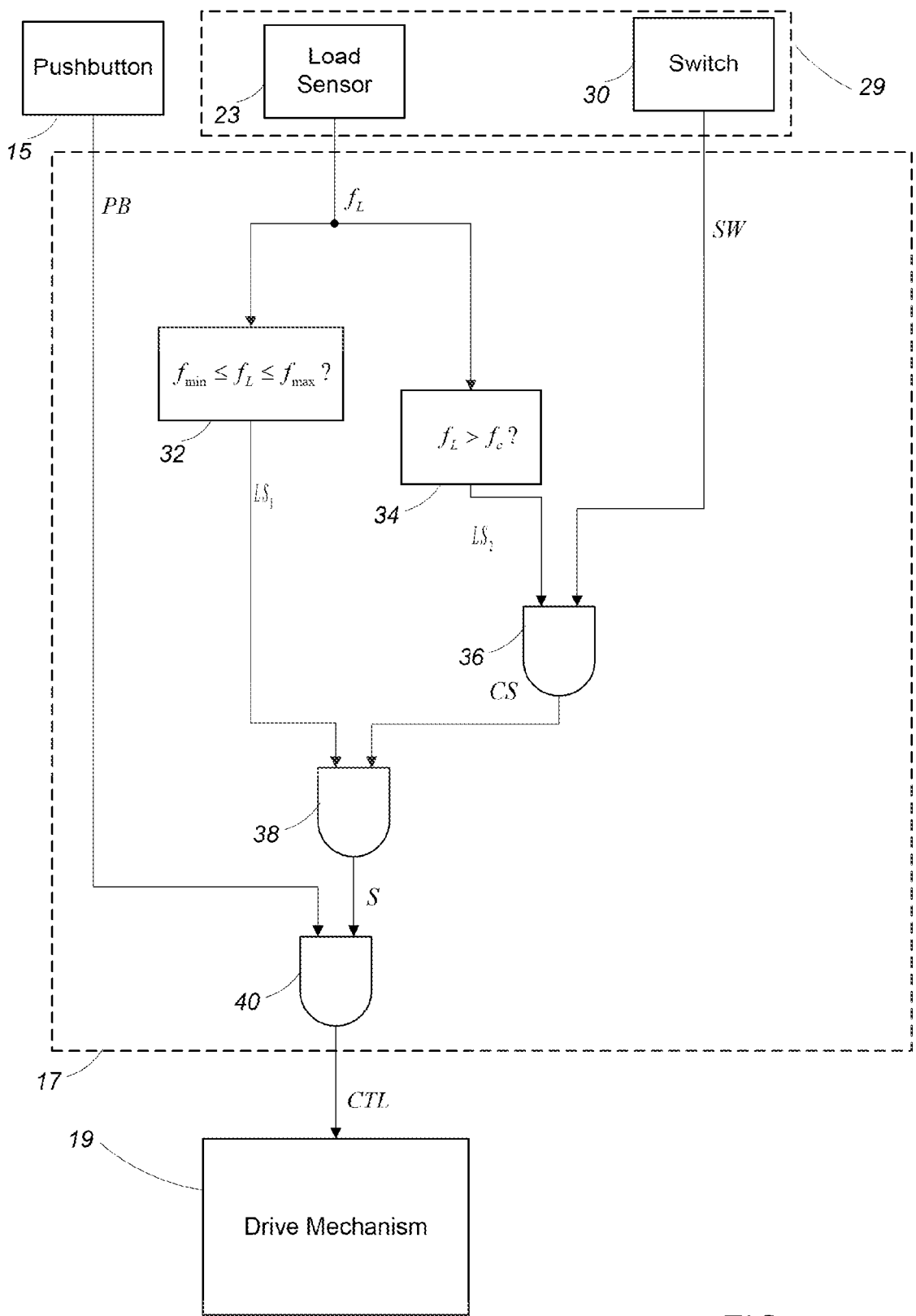
FIG. 4 schematically illustrates an algorithm implemented by control circuitry for an active injection guide.

Referring to FIG. 4, one example of the control circuitry 17 receives an input signal, PB from the pushbutton 15, and input signal, $f_L$ from the load sensor 23, and an input signal, SW from the switch 30 coupled to a surface contact sensor such as the first and second cleats 25a, 25b and processes the received input signals to generate a drive mechanism control signal, CTL. In some examples, the input signal, PB from the pushbutton 15 is a logic '1' if the pushbutton 15 is depressed and a logic '0' if the pushbutton 15 is not depressed. Similarly, the input signal, SW from the switch 30 may be a logic '1' if the switch 30 is closed (e.g., the first and second cleats 25a, 25b are depressed), and may be a logic '0' if the switch 30 is open (e.g., the first and second cleats 25a, 25b are not depressed). The input signal, $f_L$ from the load sensor 23 may have a value or magnitude characterizing a force applied along the injection axis 27 by the nozzle 14 to the target injection surface.

The control circuitry 17 may perform a first test 34 on the input signal, $f_L$ from the load sensor 23 to determine whether the instantaneous contact force along the injection axis 27 characterized by $f_L$ is greater than or equal to a contact force, $f_c$, such as a minimum or predetermined contact force selected for proper operation of the injector 10. If $f_L$ is greater than or equal to $f_c$, then the first test 34 may output a logic '1' indicating that the nozzle 14 is in contact with the target injection surface. Otherwise, if $f_L$ is less than $f_c$, then the first test 34 may output a logic '0' indicating that the nozzle 14 is not in contact with the target injection surface.

The minimum load detection may be used to detect a point of contact with a target surface, and may be combined, for example, with other contact sensors to establish a desired planar or other contact between the injector 10 and a target injection surface. Thus, the output of the first test 34, $LS_1$ and the input signal, SW from the switch 30 coupled to other contact sensors may be provided to a first AND operation 36 which generates a contact sensor output signal, CS indicative of a desired three-dimensional contact with a target injection surface. The contact sensor output signal, CS may be a logic '1' if $f_L$ is greater than or equal to $f_c$ AND SW is a logic '1' (i.e., when the nozzle 14 and both cleats 25a, 25b are in contact with the target injection surface). Otherwise, the contact sensor output signal, CS may be a logic '0.'

The algorithm implemented in the control circuitry 17 may also perform a second test 32 on the input signal, $f_L$ from the load sensor 23 to determine whether the instantaneous contact force along the injection axis 27, and indicated by the input signal, $f_L$ is greater than or equal to a minimum deformation force, $f_{min}$ and also less than or equal to a maximum deformation force, $f_{max}$. If $f_L$ is greater or equal to the minimum deformation force, $f_{min}$ and also less than or equal to the maximum deformation force, $f_{max}$, the second test 32 outputs a logic '1' indicating that the force on the load sensor, $f_L$ is within the predetermined range of deformation forces, e.g., forces sufficient to contact and deform the skin in a manner suitable for injection without being excessive. Otherwise, the second test 32 may output a logic '0' indicating that the force on the load sensor, $f_L$ is outside of the predetermined range of deformation forces.

It will be understood that other arrangements of sensors and control logic may also or instead be used to detect suitable injection conditions. For example, for certain injection types, there may be no practical upper limit on appropriate force along the injection axis 27, in which case only a lower boundary ($f_{min}$) may be used to create the output of the first test, $LS_1$ (for appropriate instantaneous contact force along the injection axis 27). In other embodiments, the contact sensors may include three or more individual contact sensors, and proper orientation of the injector 10 can be evaluated with a need for the input signal, $f_L$ from the load sensor 23.

The output of the first AND operation 36, CS (which generally evaluates multi-point contact as a proxy for correct planar orientation) and the output of the second test 32, $LS_2$ (which generally evaluates load along the injection axis 27) may be provided to a second AND operation 38 which generates a sensor output signal, S indicative of a desired physical state for an injection. The sensor output signal, S may be a logic '1' if all of the conditions for injection are met, e.g., when CS AND LS have a logic '1' value (e.g., if $f_L$ is greater or equal to $f_{min}$ and is less than or equal to $f_{max}$ AND $f_L$ is greater than or equal to $f_c$ AND SW is a logic '1'). That is, the sensor output signal, S is a logic '1' if the injector head 13 of the injector 10 is properly seated on the target injection surface 42 so that the injection axis is properly globally oriented, while at the same time a sufficient (but not excessive) axial force is applied along the injection axis 27. The first condition encourages proper axial orientation to facilitate more accurate control of injection depth. The second condition encourages proper applied force so that a localized area 44 of the target injection surface 42 is properly deformed, e.g., into a normal orientation with the injection axis 27, and with sufficient contact force to prevent slippage, rolling, or other movement of the injector head 13 along the target injection surface 42 during an injection. By concurrently enforcing these dual requirements, the injector 10 can advantageously facilitate a more accurate and consistent injection and an improved user experience.

In one aspect, the input signal, PB from the pushbutton 15 and the sensor output signal, S are provided to a third AND operation 40 which generates the control signal, CTL that controls the drive mechanism 19. The control signal, CTL may be a logic '1' if the sensor output signal, S is a logic '1' AND the input signal, PB from the pushbutton 15 is a logic '1,' where CTL being a logic '1' causes the drive mechanism 19 to perform (or initiate the performance of) an injection operation. That is, in one embodiment, an injection operation may be conditioned on proper seating of the injector head 13 on the target injection surface 42 (e.g., S is a logic '1') and a user activation of the pushbutton 15 (e.g., PB is a logic '1'). It will be understood that numerous other injection control strategies may be employed based on this general approach. For example, an injection may also or instead be automatically initiated when contact and load conditions are met. In another aspect, user activation with the pushbutton 15 may further be predicated on a dwell time or other similar window during which the other injection conditions are met. That is, the injector 10 may require that orientation and axial force be maintained for some predetermined duration (e.g., one or two seconds) before an injection is initiated, which condition may be applied independent from or after activation of the pushbutton 15.

The above-described algorithm can be implemented in discrete logic, on dedicated processing circuitry (e.g., a field-programmable gate array, custom processor or the like), as a computer program executing on a general-purpose processor (e.g., a microcontroller or microprocessor), or as any combination of these. It is noted that the terminology logic '1' and logic '0' is analogous to the TRUE and FALSE states, respectively in a computer program. It should also be appreciated that equivalent process flows or logical constructs exist, and that any other logic, program instructions or the like suitable for achieving the desired results may also or instead be employed.

4 EXAMPLES

Figure 5A:
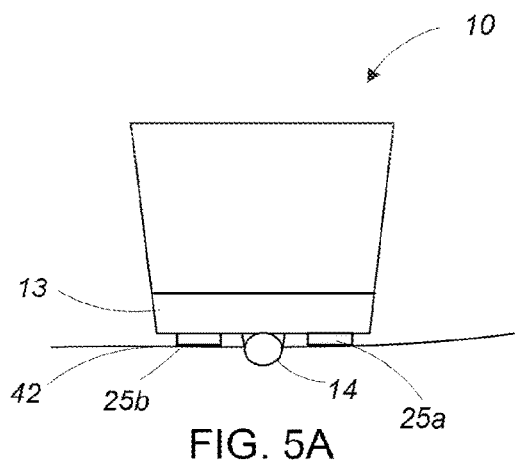
FIGS. 5A and 5B show a front view and side view, respectively of the injector of FIG. 1 properly seated on a target injection surface.
Figure 5B:
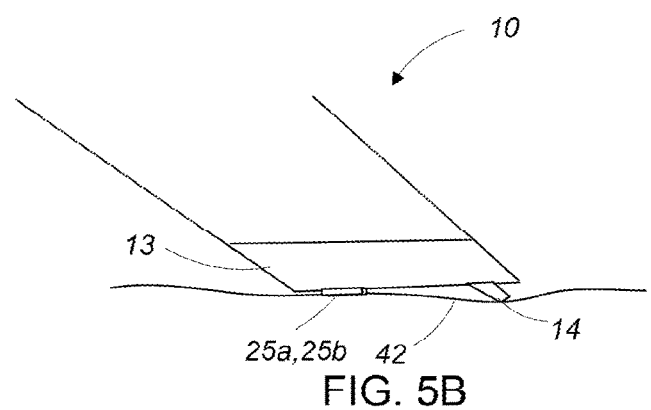

Referring to FIGS. 5A and 5B, a front view and a side view, respectively of the injector 10 shows the injector head 13 properly seated on the target injection surface 42 with both cleats 25*a*, 25*b* and the nozzle 14 in contact with the target injection surface 42 (and with the force exerted by the nozzle 14 along the injection axis 27 being in the predetermined range of deformation forces). In the scenario shown in FIGS. 5*a* and 5*b*, the sensor output signal, S output from the second AND operation 38 is a logic '1.' If a user activates the pushbutton 15, the input signal, PB from the pushbutton 15 changes to a logic '1,' causing the CTL signal output from the third AND operation 40 to change to a logic '1.' When the CTL signal output from the third AND operation 40 changes to a logic '1,' the drive mechanism 19 activates (after a delay, where appropriate) to initiate and perform an injection operation. Of course, if the force exerted by the nozzle 14 along the injection axis 27 is not within the predetermined range of deformation forces, the CTL signal output will remain at a logic '0' and an injection will not be initiated, even when the pushbutton 15 is depressed.

Figure 5C:
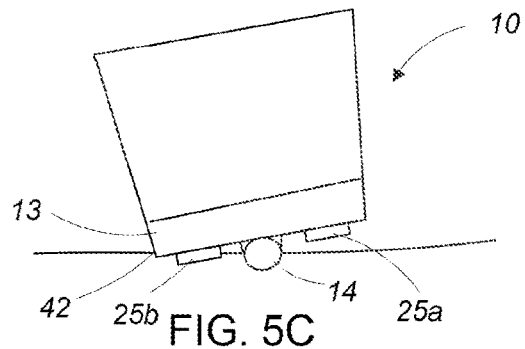
FIG. 5C shows front view of the injector of FIG. 1 in a first improperly seated scenario.

Referring to FIG. 5C, a front view of the injector 10 shows the injector head 13 improperly seated on the target injection surface 42 with the first cleat 25*a* out of contact with the target injection surface 42, resulting in a misaligned injection axis 27. Because the first cleat 25*a* is out of contact with the target injection surface 42, the input signal, SW from the switch 30 is a logic '0,' preventing the CTL signal output from the third AND operation 40 from changing to a logic '1.' As such, no injection operation can be performed.

Figure 5D:
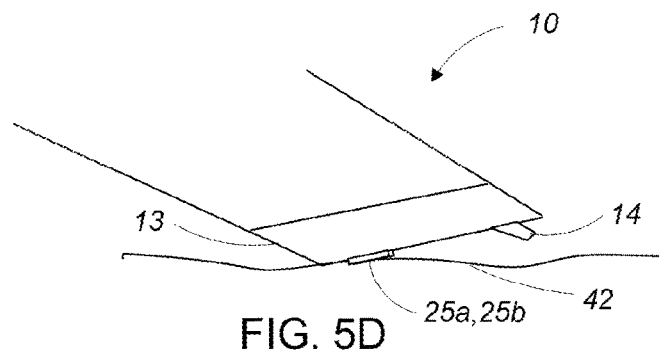
FIG. 5D shows side view of the injector of FIG. 1 in a second improperly seated scenario.

Referring to FIG. 5D, a side view of the injector 10 shows the injector head 13 improperly seated on the target injection surface 42 with the nozzle 14 out of contact with the target injection surface 42, resulting in a misaligned injection axis 27. Because the nozzle 14 is out of contact with the target injection surface 42, the first test 34 outputs a logic '0,' preventing the CTL signal output from the third AND operation 40 from changing to a logic '1.' As such, no injection operation can be performed.

Figure 5E:
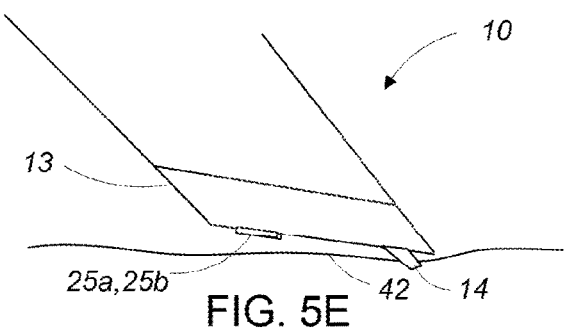
FIG. 5E shows side view of the injector of FIG. 1 in a third improperly seated scenario.

Referring to FIG. 5E, a side view of the injector 10 shows the injector head 13 improperly seated on the target injection surface 42 with the first cleat 25*a* and the second cleat 25*b* out of contact with the target injection surface 42, resulting in a misaligned injection axis 27. Because the first cleat 25*a* and the second cleat 25*a* are out of contact with the target injection surface 42, the input signal, SW from the switch 30 is a logic '0,' preventing the CTL signal output from the third AND operation 40 from changing to a logic '1.' As such, no injection operation can be performed.

Figure 6:
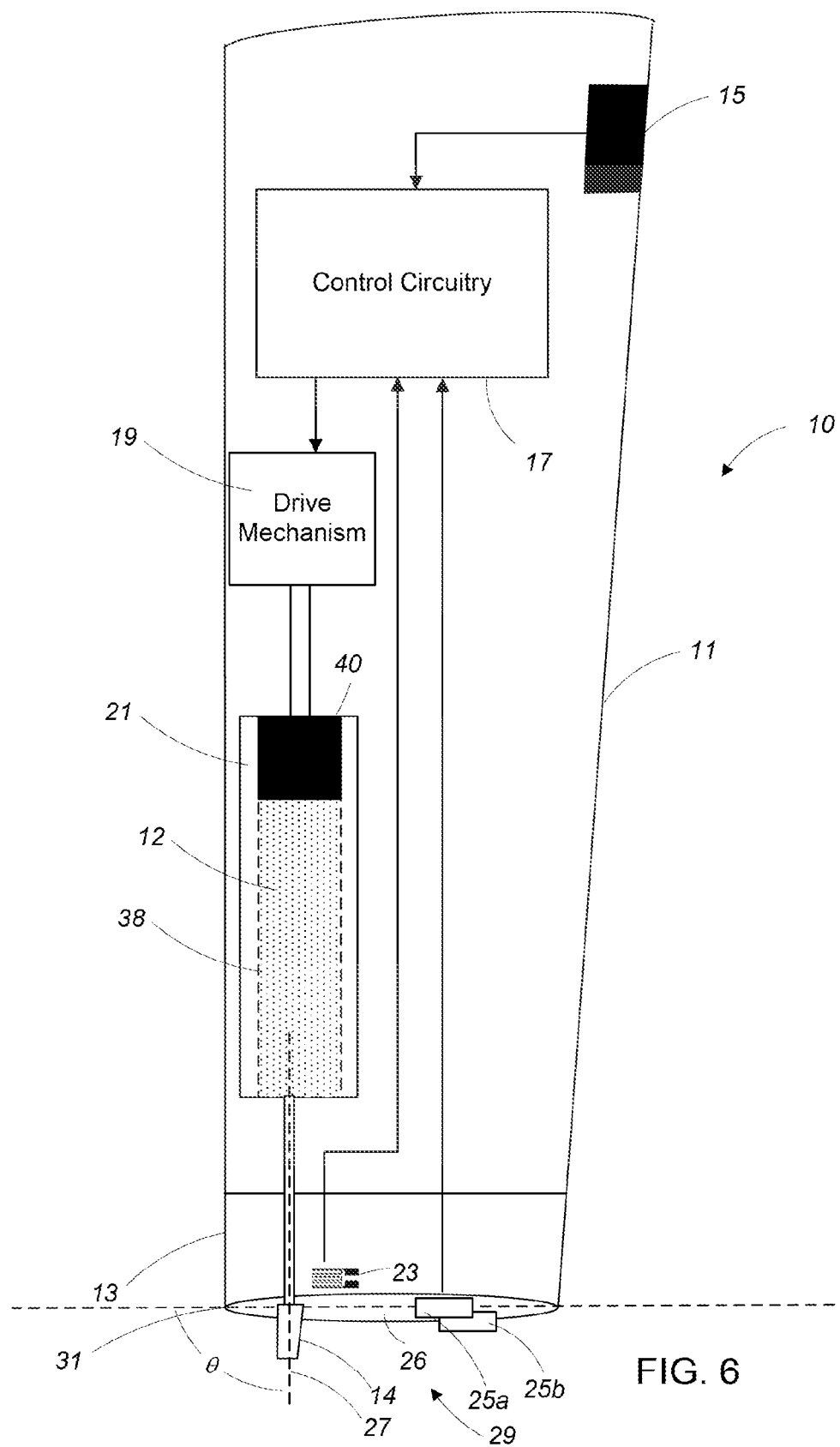
FIG. 6 shows a needle-free injector with an active injection guide.

FIG. 6 shows a needle-free injector with an active injection guide. In some examples the angle, θ between the injection axis 27 and the contact surface 20 is an acute angle. In other embodiments the angle, θ is a 90° angle. For example, referring to FIG. 6, in an alternative embodiment of the injector 10, the angle, θ between the injection axis 27 and the contact surface 20 is a 90° angle. In this configuration, it may still be useful to independently measure global axis orientation (via an array of contact sensors) and axial load along the injection axis (via a load sensor) and use these measurements as conditions for initiating an injection. In other examples, the injection guide may omit the force sensor attached to the nozzle and only use a plurality of placement sensors (e.g., three cleats attached to one or more switches), which may also individually or collectively measure an axial load.

Figure 7:
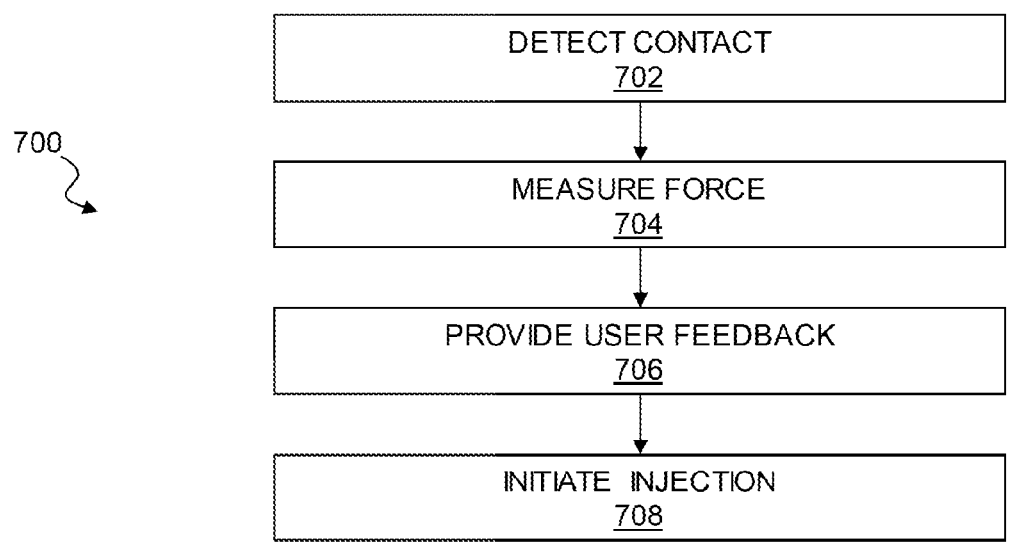
FIG. 7 is a flow chart of a method for operating an active injection guide.

FIG. 7 is a flow chart of a method for operating an active injection guide. The method 700 may be used, for example, to guide an injection device such as any of the injectors described herein so that the injection device is properly situated before an injection can be initiated.

As shown in step 704, the method 700 may begin with detecting a contact and/or an orientation between a contact surface of an active injection guide and a target surface such as a patient's skin. In general, these may be independent measurements, a common measurement, or some combination of these, and any of the techniques described herein, or any other suitable techniques for detecting contact and measuring orientation as predicates for an injection as contemplated herein may also or instead be used to detect the contact and orientation. For example, detecting the contact may include detecting contact between a contact surface of the injection guide and the target surface using a contact sensor such as any of the contact sensors described herein. Similarly, detecting the orientation between the contact surface of the active injection guide and the target surface may include detecting the orientation using any of the contact sensors or other sensors or the like as described herein.

As shown in step 704, the method 700 may include measuring a force along an injection axis for the injection device. In one aspect, the injection axis may be at an acute angle relative to the target surface when the contact surface is in planar contact with the target surface. In another aspect, the injection axis may be normal to the contact surface. Measuring the force may, for example, include measuring an instantaneous contact force using a load sensor or any of the other sensors or sensor systems described herein. In one aspect, this measurement may occur concurrently with the detection of contact in step 702. In another aspect, this may include measuring the force along the injection axis in response to detecting the contact between the contact surface and the target surface in step 702. More generally, the respective measurements of contact and the contact force may be taken substantially continuously, or alternately, or responsively, e.g., where one of the measurements is repeated until the result falls within a predetermined range, or above or below a predetermined threshold, and then the other measurement is taken. Where the same sensors are used for both measurements, the respective measurements may be concurrently taken. In another aspect, multiple individual measurements of an instantaneous contact force may be taken at different locations about a contact region (e.g., the contact surface, or a region about and/or within the contact surface) and resolved into a force vector including a magnitude and a direction of the contact force. This may, in turn, be resolved using basic geometric calculations to calculate the normal or axial contact force for an injector, or an injection axis of the injector.

It will be understood that the above sensor measurements are useful as a proxy for proper seating of an injection device for an injection. Thus, the method 700 may include causing, by an injection protrusion extending along the injection axis, a predefined deformation of the target surface, which occurs in response to (or stated differently, as a consequence of) the contact sensor detecting the contact between the contact surface and the target surface and the load sensor measuring a target force in a predefined range of forces along the injection axis.

As shown in step 706, the method 700 may include providing user feedback from the injection device, for example, when the orientation and the force are within predetermined ranges suitable for injection or after the orientation and the force remain within the predetermined ranges for a predetermined duration, e.g. one or two seconds. In addition to orientation of the injection device, an orientation of the applied surface may be used, e.g., by evaluating whether a three-dimensional direction of force applied by the injection device to a target surface is within a suitable range for injection. User feedback may, for example, include a visual output, an audio output, a haptic output, or any combination of these.

As shown in step 708, the method 700 may include initiating an injection from the injection device. This may include any automatic, semi-automatic or manual technique for initiating an injection subject to the orientation and load conditions described herein. For example, this may include automatically initiating an injection from the injection device when the orientation and the force are within predetermined ranges suitable for injection. In a semi-automatic embodiment, this may include providing feedback to the user that the orientation and the force are within suitable ranges, and then awaiting a confirmation input from the user. In a manual embodiment, this may include responding to a manual input, subject to the orientation and force constraints (and optionally, time constraints) discussed above.

The method 700 may include additional steps, such as monitoring after an injection is initiated to ensure that the correct physical posture of the injection device is maintained. The steps may also be modified or re-ordered without departing from the scope of this disclosure.

Figure 8:
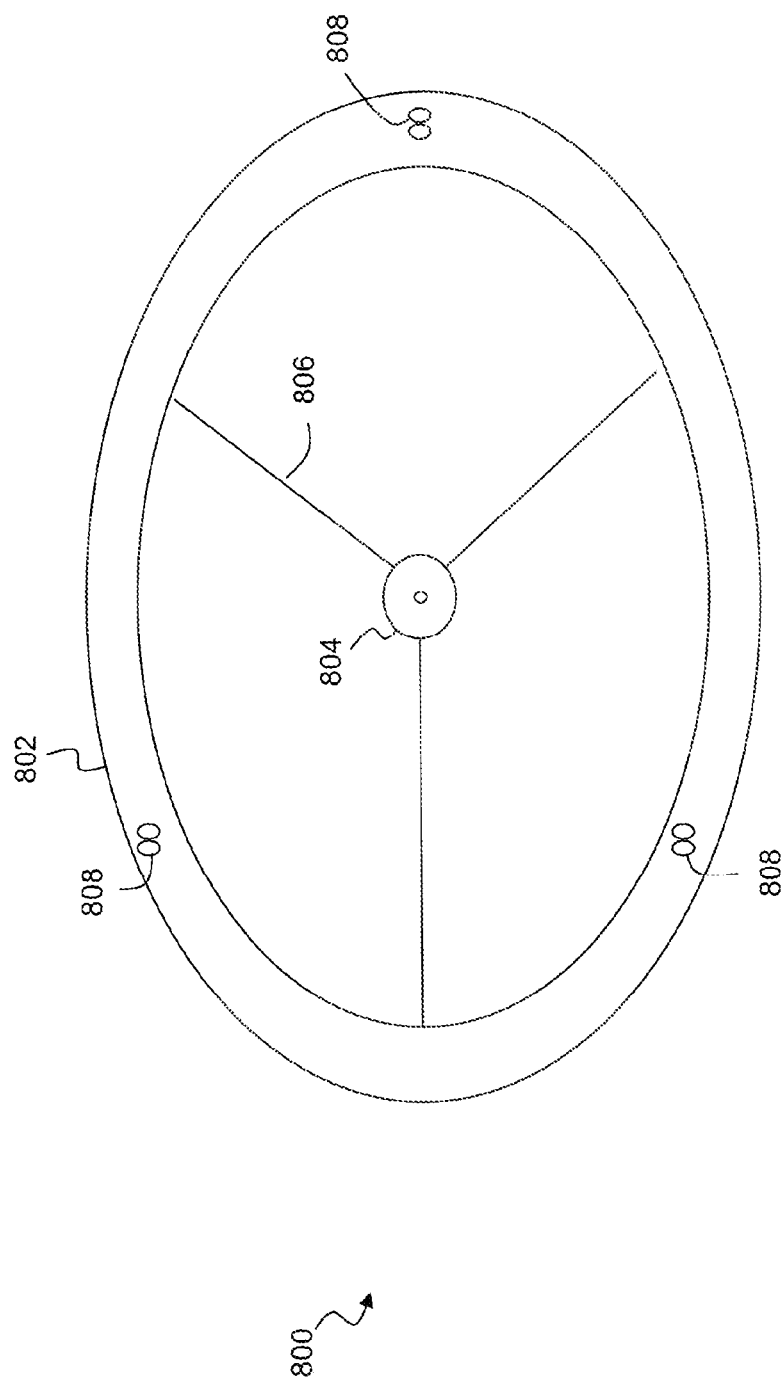
FIG. 8 shows a top view of a sensor arrangement for an injection guide.

FIG. 8 shows a top view of a sensor arrangement for an injection guide. In general, a guide 800 may have a contact surface 802 such as a planar oval, circle or the like coupled to an injection nozzle 804 through any suitable structure 806 and oriented relative to the injection nozzle 804 for placement against a target surface in a manner that aligns the injection nozzle 804 to a desired injection trajectory into the target surface. The contact surface 802 may, for example, include multiple pairs of sensors 808, each having a contact switch with a different load threshold. Thus for example, one of the pairs of sensors 808 may have a first sensor that detects a load of at least three Newtons and a second sensor that detects a load of at least five Newtons. Together, this pair of sensors 808 can detect ranges of force, e.g., a normal force on the contact surface 802 of between 3-5 Newtons. By measuring a range bound contact force at a number of locations about the contact surface 802, this arrangement of contact switches can be used to ensure that an injector has a proper planar alignment (e.g., the contact surface 802 is in contact at three or more locations within a plane or along some other 3D surface) and a load along an axis of the injection nozzle 804 within some suitable, predetermined range. As a significant advantage, this type of arrangement also permits the calculation or estimate of off-axis loading in order to evaluate whether the angle of applied force, relative to the target surface, is suitable for injection. More generally, any number and arrangement of force-sensitive switches or sensor having varying trigger points or thresholds may be suitably deployed as a detection system to concurrently measure alignment and axial load as contemplated herein.

As noted above, in another aspect, the detection system may usefully measure the angle of applied force instead of, or in addition to, the axial load. For example, the location and magnitude of a number of point loads may be used to resolve the three-dimensional direction and magnitude of an instantaneous contact force applied by the injection device to the target surface. In another aspect, it will be appreciated that a normal load, e.g., normal to the target surface, or normal to an injector body in embodiments where the injection axis is at an angle to the injector body, may also or instead be measured, either as a proxy for axial load or as an alternative threshold for initiating an injection.

Still more generally, various combinations of sensor types and arrangements may be used to measure both axial load and three-dimensional alignment, either separately or in combination. For example, a load sensor that measures force along the injection axis may include one or more contact sensors for measuring point contact or planar contact/orientation, and a contact sensor that detects orientation may include one or more load sensors for measuring an axial load. All such combinations are intended to fall within the scope of this disclosure unless a more specific configuration is explicitly recited or otherwise clear from the context.

According to the foregoing, it will be understood that the various load sensors and contact sensor described herein may include force sensors, pressure sensors, capacitive sensors, or any other sensors or combination of sensors usefully for concurrently measuring axial load and three-dimensional alignment as contemplated herein.

5 ALTERNATIVES

In some examples, the contact sensor 52 may comprise a plurality of placement sensors, such as three or more sensors suitable for resolving planar alignment in three dimensions, which may be used in addition to, or instead of, a load sensor 50 for detecting proper seating of the injector head. In some examples, instead of or in addition to the cleats, switches and load sensors used in the embodiments above, the contact sensors 29 may use a variety of contact sensing modalities, including but not limited to capacitive sensing, electrical impedance sensing or other electrical modalities. Contact sensors 52 may also or instead incorporate other components that are sensitive to orientation and movement, including accelerometers and gyroscopes.

Though for the embodiments described above, the focus has been on needle-free injectors, it is understood that proper axial orientation can also be important for needle-based injector systems, to ensure that a defined angle of entry is maintained, and that undue stress is not placed on the needle. Such additional stress for needle-based systems could lead to tissue damage or even needle breakage. It should be understood that the core elements of the instant invention also apply to needle-based systems.

In some examples, the injector is configured to provide feedback to the user to let them know when the injector head is properly seated on the target injection surface. For example, the injector may include a feedback device such as a visual, audio, or haptic feedback device that is activated when the injector head is properly seated.

The detection of a suitable injection state (e.g., planar orientation and axial load) may also or instead be used as a control input for other injector functions. For example, the injector may automatically initiate an injection when the injector head is properly seated on the target injection surface. This may be used in combination with other inputs and outputs. For example, such an automatic injection may only be initiated after the proper injection state is maintained for a predetermined duration such as one or two seconds, or only when a user is also depressing the injection button. In another aspect, the injector may, after detecting a proper injection state, create a user alert such as a beep or a buzz to notify the user that an injection will occur in a few moments. The user may be provided with more detailed information. For example, the proper alignment may be indicated with a buzz, and then a countdown to an injection may be signaled with several one second beeps or any other suitable signal. In another aspect, an LED display or the like may provide a countdown timer or other signal to a user indicating that an injection is about to begin. Similarly, the injection state may be used to terminate an injection. For example, the injector may automatically terminate an injection operation after the injection has begun but before the injection is complete if the injector head is no longer properly seated on the target injection surface.

Also as noted above, while the axial load can usefully be employed as a criterion or threshold for initiating an injection, a more general magnitude and direction of the force applied by the injection device may also or instead be employed, either as a proxy for the axial load, or as a separate criterion, e.g., for evaluating whether the direction of the applied force is within a suitable range for initiating an injection.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes, such as random access memory associated with a processor, or a storage device such as a disk drive, flash memory or any other optical, electromagnetic, magnetic, infrared or other device or combination of devices.

It will be appreciated that the devices, methods and systems described above are set forth by way of example and not of limitation. Numerous variations, additions, omissions, and other modifications will be apparent to one of ordinary skill in the art. Absent an explicit indication to the contrary, the disclosed steps may be modified, supplemented, omitted, and/or re-ordered without departing from the scope of this disclosure. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:
1. An active injection guide comprising:
an injector having an injection axis;
a contact surface configured to be placed on a target surface for an injection of an injectate into the target surface from the injector;
a sensor arrangement including sensors from a set of three or more sensors, wherein each of the sensors from the set of three or more sensors has a plurality of load thresholds,
wherein the sensors from the set of three or more sensors are coupled to the contact surface and spaced around the injection axis, wherein each of the sensors from the set of three or more sensors is configured to measure a contact force against the target surface along the injection axis; and
a controller configured
to receive concurrent measurements from the sensors from the set of three or more sensors,
to use the concurrent measurements from the sensors from the set of three or more sensors
to generate an orientation of the injector relative to the target surface and the contact force against the target surface along the injection axis and
to determine, for each of the three or more sensors, whether the contact force on the sensors from the set of three or more sensors is within a predetermined range that is suitable for the injection, the predetermined range being between the plurality of load thresholds of each sensor from the set of three or more sensors, and to prevent activation of the injector until the generated orientation and the generated force against the target surface are each within predetermined ranges suitable for the injection, wherein the injector is a needle-free injector.

2. The active injection guide of claim 1, further comprising a feedback device configured to provide user feedback when the orientation and the force against the target surface are within the predetermined ranges suitable for the injection.

3. The active injection guide of claim 2, wherein the feedback device includes at least one visual device.

4. The active injection guide of claim 1, wherein said set of three or more sensors comprise a load sensor that is mechanically coupled to a nozzle of said injector and sensors that are at two spatially separated contact points and wherein the sensors that are at the two spatially separated contact points and the load sensor are arranged in a triangular pattern on the contact surface.

5. The active injection guide of claim 1, wherein the controller is configured to automatically initiate the injection when the orientation and the force against the target surface are within the predetermined ranges suitable for the injection.

6. The active injection guide of claim 1, wherein the controller is configured to terminate the injection after the injection is initiated if the orientation or the force against the target surface falls outside the predetermined ranges suitable for the injection during the injection.

7. The active injection guide of claim 1, wherein the set of three or more sensors comprise a contact sensor and a load sensor, said injection guide further comprising a processor configured to calculate the orientation and the force against the target surface based on signals from the contact sensor and from the load sensor.

8. The active injection guide of claim 1, wherein one sensor from said set of three or more sensors is a load sensor that is mechanically coupled to a nozzle of said injector and wherein the load sensor is configured to contact an injection protrusion on the contact surface and is configured to detect an instantaneous contact force between the load sensor and the injection protrusion.

9. The active injection guide of claim 1, wherein the set of three or more sensors comprise a load sensor and a contact sensor, wherein the load sensor is mechanically coupled to a nozzle of said injector, wherein the contact sensor is configured to detect contact between the contact surface and the target surface, and wherein the load sensor is configured to measure a target force in a predefined range of forces along the injection axis.

10. The active injection guide of claim 1, wherein the three or more sensors of the sensor arrangement comprise a load sensor and a contact sensor that is spatially separated from the load sensor.

11. The active injection guide of claim 1, wherein at least one of the three or more sensors of the sensor arrangement comprises an electrical impedance measuring sensor including a plurality of spatially separated electrically conductive contact points.

12. The active injection guide of claim 1, wherein at least one of the three or more sensors of the sensor arrangement comprises one or more mechanical switches.

13. The active injection guide of claim 1, wherein at least one of the three or more sensors of the sensor arrangement comprises a capacitive sensor.

14. The active injection guide of claim 1, further comprising a load sensor that is mechanically coupled to a nozzle of said injector, wherein the load sensor comprises a strain gauge.

15. The active injection guide of claim 1, wherein the controller is configured to prevent the activation of the injector when the force against the target surface is below a predetermined range of force and also to prevent the activation of the injector when the force against the target surface is above the predetermined range of force.

16. The active injection guide of claim 1, wherein at least one of the three or more sensors in the sensor arrangement is configured to provide a binary indication that a threshold for the contact force at the one of the at least one of the three or more sensors exceeds a predetermined threshold.

17. The active injection guide of claim 1, wherein each of the three or more sensors of the sensor arrangement is configured to respond to a load exceeding a predetermined limit by providing a binary indication that a threshold for the contact force has exceeded the predetermined limit.

18. The active injection guide of claim 1, wherein at least one of the three or more sensors of the sensor arrangement includes at least one contact switch with a load threshold.

19. The active injection guide of claim 1, wherein two of the sensors comprise contact switches with different load thresholds.

20. The active injection guide of claim 1, wherein six of the sensors of the sensor arrangement comprise mechanical switches.

* * * * *